US00PP29660P3

(12) United States Plant Patent
Suphachadiwong

(10) Patent No.: US PP29,660 P3
(45) Date of Patent: Sep. 11, 2018

(54) *VANDA* PLANT NAMED 'SPCDW1603'

(50) Latin Name: ***Vanda* spp. Jones ex R. Br.**
Varietal Denomination: SPCDW1603

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/731,666

(22) Filed: Jul. 13, 2017

(65) Prior Publication Data

US 2018/0020593 P1 Jan. 18, 2018

(30) Foreign Application Priority Data

Jul. 14, 2016 (QZ) ..... PBR 2016/1792

(51) Int. Cl.
*A01H 5/02* (2018.01)

(52) U.S. Cl.
USPC ..... Plt./311

(58) Field of Classification Search
USPC ..... Plt./311
CPC ..... A01H 5/02; A01H 6/62
See application file for complete search history.

*Primary Examiner* — June Hwu
(74) *Attorney, Agent, or Firm* — Samuel R. McCoy, Jr.

(57) ABSTRACT

A new and distinct *Vanda* cultivar named 'SPCDW1603' which is characterized by a small plant size with relatively large flowers, a light violet dorsal sepal and light violet lateral petals which are all heavily dotted purple, cream colored lateral sepals which are densely dotted and blotched purple, a labellum with a dark purple central lobe and cream coloured lateral lobes which are dotted purple, a cream colored column which is lightly suffused with purple, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1603'.

CROSS REFERENCE TO RELATED APPLICATIONS

This application claims priority to the Community Plant Variety Rights application number 2016/1792, filed Jul. 14, 2016, which is herein incorporated by reference.

BACKGROUND OF THE INVENTION

Parentage: The *Vanda* variety 'SPCDW1603' is the result of a planned breeding program. The new variety originated as a seedling from the crossing of *Vanda* 'M40C2' (not patented), the seed parent, with *Vanda* 'K75' (not patented), the pollen parent. Both parents were developed by, and are owned by, the inventor and were never commercially released. The crossing was made by the inventor in his research greenhouse in Bangphra, Thailand in January of 2005.

The new variety was first selected in December of 2008, in a research greenhouse in Bangphra, Thailand belonging to the inventor. After identifying the new variety as a potentially interesting selection, the inventor continued confidential testing and propagation of 'SPCDW1603', assessing stability of the unique characteristics of this variety.

Asexual Reproduction: Asexual reproduction of the new cultivar 'SPCDW1603', by way of mericloning, was first initiated in February of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1603' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1603'. These characteristics in combination distinguish 'SPCDW1603' as a new and distinct *Vanda* cultivar:

1. *Vanda* 'SPCDW1603' exhibits a small plant size and relatively large flowers; and
2. *Vanda* 'SPCDW1603' exhibits a light violet dorsal sepal and light violet lateral petals, all of which are heavily dotted purple; and
3. *Vanda* 'SPCDW1603' exhibits cream colored lateral sepals which are densely dotted and blotched purple; and 4. *Vanda* 'SPCDW1603' exhibits a labellum with a dark purple central lobe and cream coloured lateral lobes which are dotted purple.
5. *Vanda* 'SPCDW1603' exhibits a cream colored column which is lightly suffused with purple.

BOTANICAL DESCRIPTION OF THE PLANT

Figure 1:
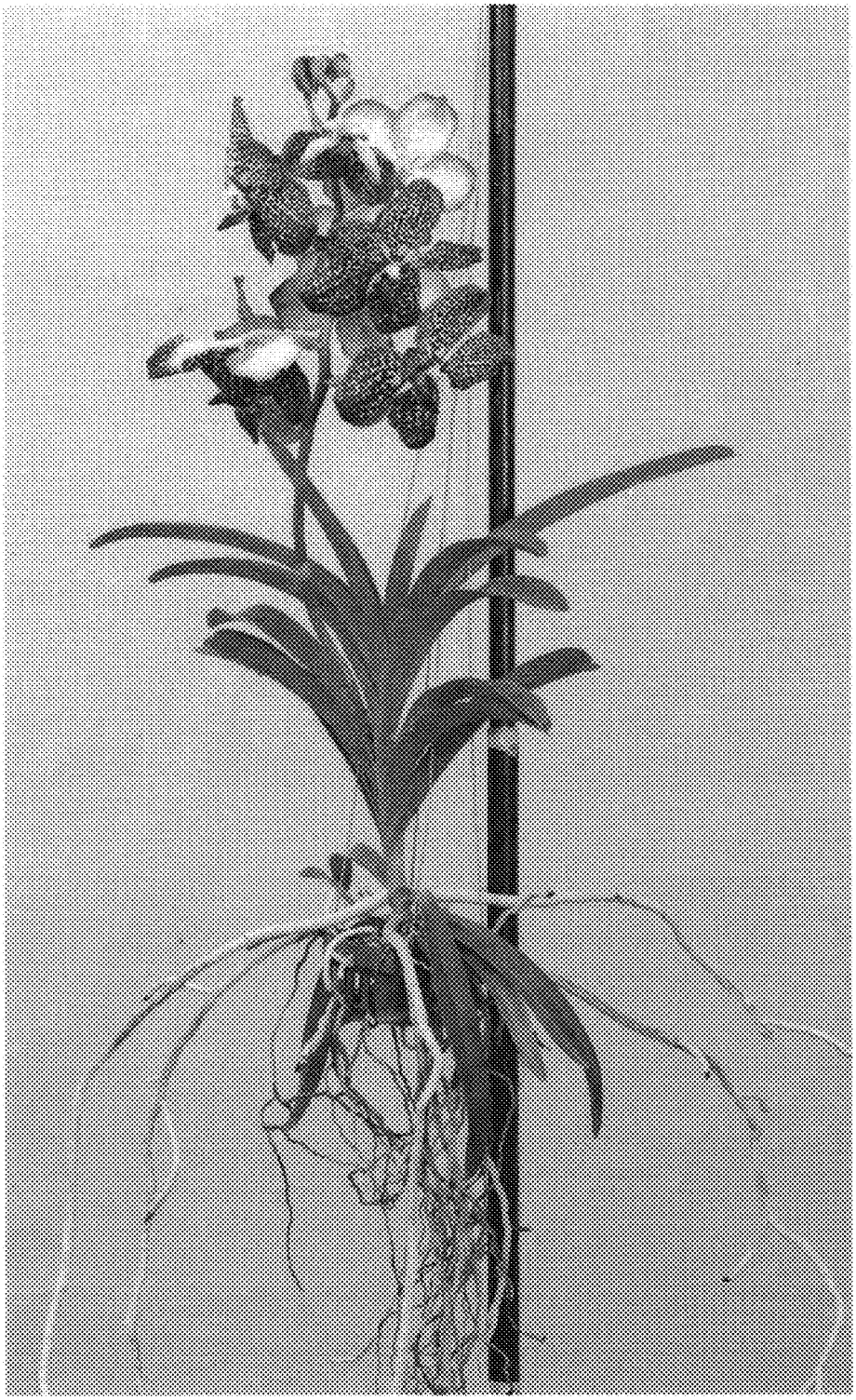
FIG. 1 illustrates, as nearly true as it is reasonably possible to make the same in color photographs of this type, an exemplary plant of 'SPCDW1603' grown in a commercial greenhouse in Honselersdijk, the Netherlands. This plant is approximately 6 years old from the time of mericloning, shown planted in an 8 by 8 cm container.
Figure 2:
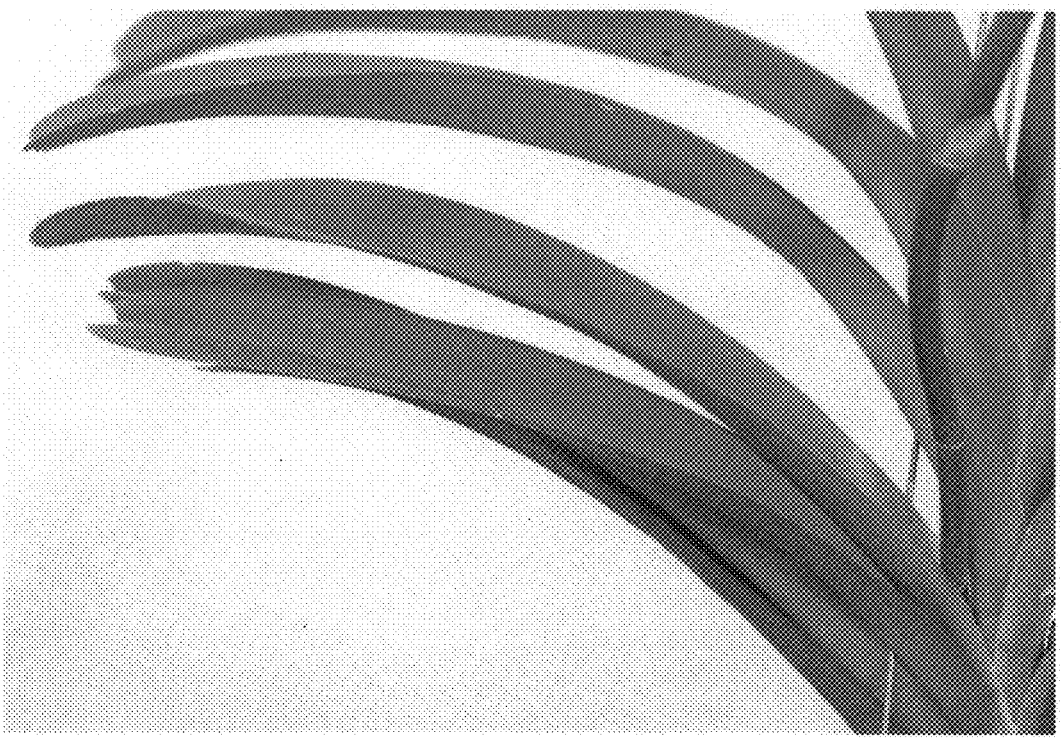
FIG. 2 illustrates, as nearly true as it is reasonably possible to make the same in color photographs of this type, the typical foliage of 'SPCDW1603'.
Figure 3:
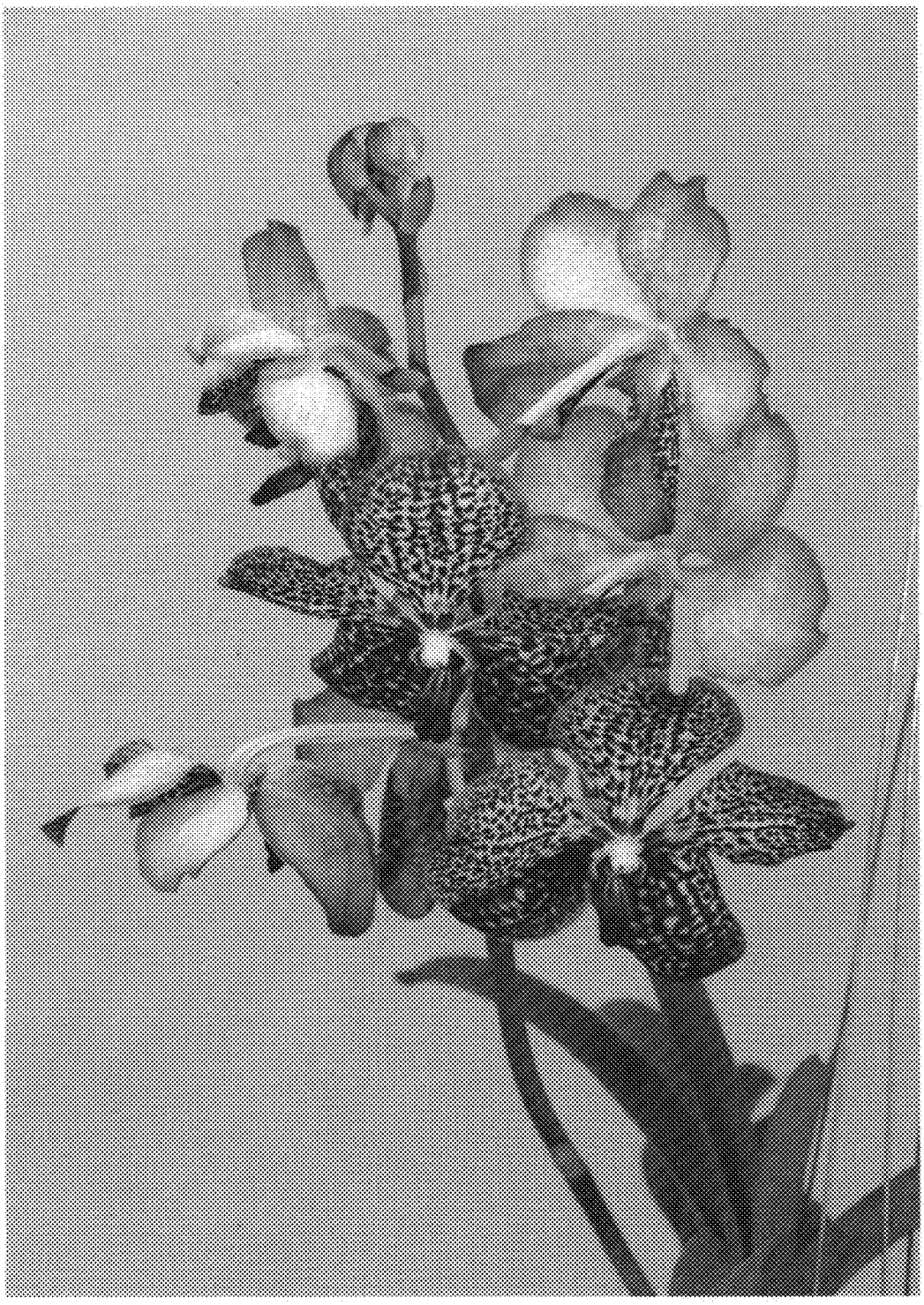
FIG. 3 illustrates, as nearly true as it is reasonably possible to make the same in color photographs of this type, the typical inflorescence of 'SPCDW1603'.
Figure 4:
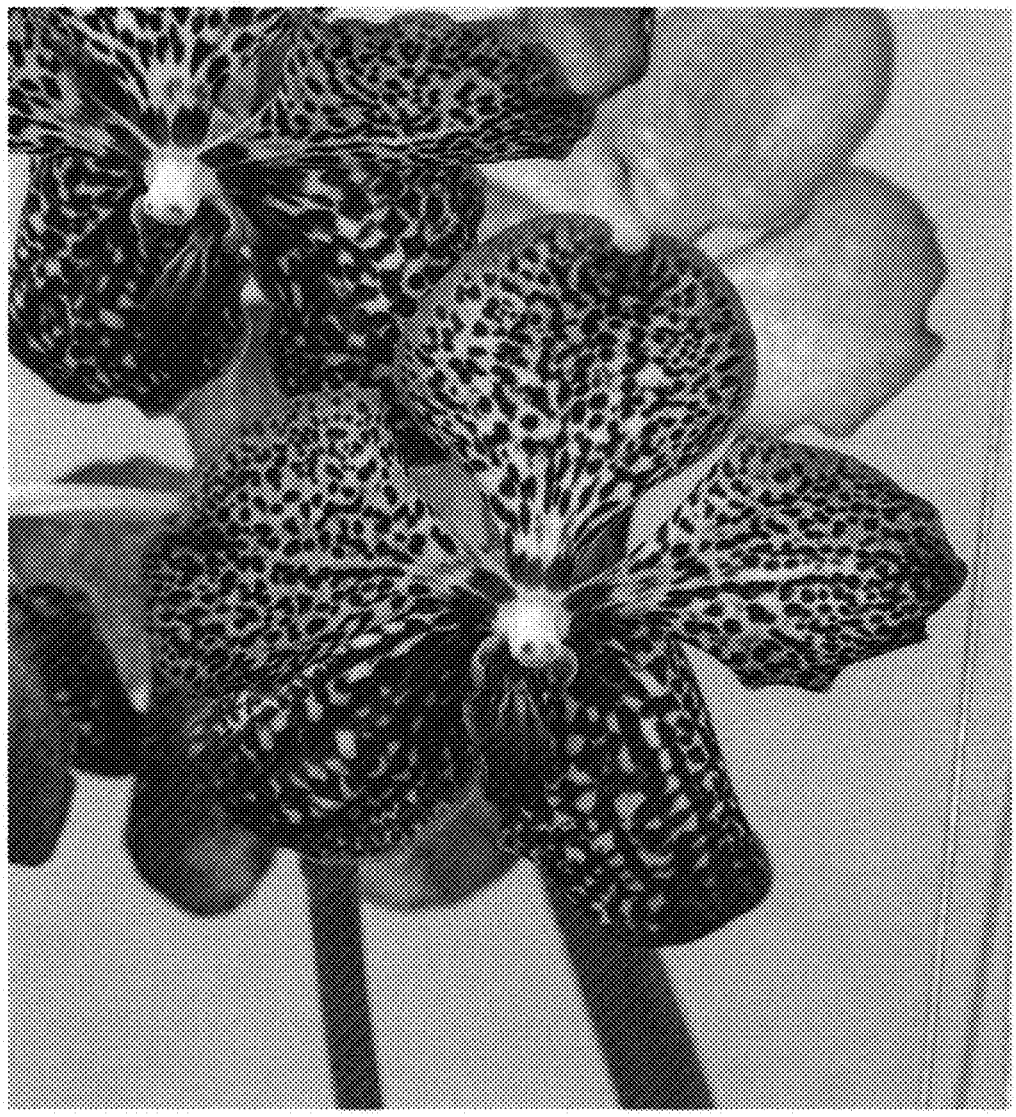
FIG. 4 illustrates, as nearly true as it is reasonably possible to make the same in color photographs of this type, the typical flower of 'SPCDW1603'.

The following observations and measurements made in June of 2017 describe averages from a sample set of six specimens of six year-old 'SPCDW1603' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1603' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1603' and comparisons with the parents and most similar commercial variety of *Vanda* are provided below.

Plant description:

*Growth habit*.—Perennial; monopodial, upright. Single monopodial leafy stem, with flowers carried slightly above the leaf plane; inflorescences growing from the leaf axils.

*Average height from base (plant grown in hanging basket, so no soil line present) to foliar plane*.—36.7 cm.

*Average height from base (plant grown in hanging basket, so no soil line present) to top of floral plane*.—47.7 cm.

*Plant spread*.—Average of 42.5 cm.

*Appropriate container size*.—8 cm by 8 cm rectangular hanging basket.

*Growth rate*.—Moderate.

*Plant vigor*.—Moderate.

*Propagation type*.—Meristematic tissue culture propagation using the base of the leaves.

*Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility*.—Plants have not been observed to be susceptible or resistant to pathogens and pests common to *Vanda*.

*Environmental tolerances*.—Adapt to, at least, USDA Zones 11 and 12 and temperatures as high as 40 degrees Celsius; high tolerance to rain; moderate to high tolerance to wind.

Root system:

*General*.—Densely rooting; with aerial roots only.

*Dimensions, mature roots*.—55.4 cm long with a diameter of 0.5 cm, on average.

*Texture*.—Very fleshy; non-fibrous.

*Color*.—Greyed-green, nearest to RHS 196D; root apex is yellow-green, RHS 146A.

Stem:

*Branching habit*.—Monopodial; no lateral branches present.

*Number of primary (main) stems per plant*.—One.

*Number of secondary (lateral) branches per plant*.—None.

*Appearance and shape*.—Circular, formed by the leaf sheaths.

*Length*.—18.0 cm.

*Diameter*.—0.8 cm.

*Internode length*.—0.4 cm.

*Luster*.—Matte.

*Aspect, main stem*.—Near vertical.

*Strength*.—Very strong.

*Color, juvenile*.—Yellow-green, nearest to RHS 145C.

*Color, mature*.—Yellow-green, nearest to RHS 145C.

*Color at internodes*.—Yellow-green, nearest to RHS 145C.

*Pubescence*.—Glabrous.

Foliage:

*Arrangement*.—Distichous.

*Dimensions*.—20.9 cm long, excluding the sheath, and 2.1 cm wide.

*Shape of blade*.—Ligulate; moderately to strongly carinate.

*Aspect*.—Slightly to moderately curved.

*Apex*.—Unequal praemorse.

*Base*.—Sheathing.

*Sheath dimensions*.—3.0 cm long and 1.1 cm wide, on average.

*Sheath color*.—Yellow-green, nearest to in between RHS 145B and 145C.

*Margin*.—Entire.

*Pubescence, texture and luster of adaxial surface*.—Glabrous, smooth, and very slightly glossy.

*Pubescence, texture and luster of abaxial surface*.—Glabrous, smooth, and matte.

*Color*.—Juvenile foliage, adaxial surface — Nearest to in between green, RHS 143A, and yellow-green, RHS 146B. Juvenile foliage, abaxial surface — Nearest to in between green, RHS 143A, and yellow-green, RHS 146B. Mature foliage, adaxial surface — Green, in between RHS 137B and 143A, and slightly darker towards the margins, nearest to RHS 137A. Mature foliage, abaxial surface — Green, nearest to RHS 143C, and darker towards the margins, nearest to in between RHS 138A and 138B.

*Venation*.—Parallel.

*Venation color, adaxial surface*.—Green, nearest to RHS N138B.

*Venation color, abaxial surface*.—Yellow-green, in between RHS 144B and 144C.

*Petiole*.—No petioles present; leaves sessile.

Inflorescence:

*Inflorescence arrangement*.—Axially placed raceme.

*Natural flowering season*.—Autumn into winter.

*Time to flower*.—Approximately 10 months.

*Flowers per inflorescence*.—Average of 11.

*Flowers per plant*.—9 open flowers and 2 flower buds.

*Inflorescence height*.—Approximately 23.8 cm (measured from base of lowest flower to top of upper flower).

*Inflorescence diameter*.—Approximately 20.6 cm.

*Peduncle*.—Dimensions — Approximately 40.0 cm long and 0.7 cm wide. Aspect — Generally at a 30 degree angle to lateral branch axis; varying between 25 and 35 degrees. Strength — Moderately strong. Texture and luster — Glabrous and moderately glossy. Color — Yellow-green, nearest to RHS 144B.

Bud:

*Length*.—Average of 1.4 cm.

*Diameter*.—Average horizontal diameter is 1.1 cm; the vertical diameter is 1.7 cm.

*Shape*.—Cubic, with a deltoid apex which is pointed downward.

*Pubescence, texture and luster*.—Glabrous, smooth and very slightly glossy.

*Color*.—Yellow-green, nearest to RHS 144C, and heavily suffused with greyed-purple at the apex, nearest to RHS N186C; dotted with greyed-purple, RHS N186C.

Flower:

*Flower type*.—Zygomorphic (orchidaceous), typical shape for the genus *Vanda*.

*Flowering habit*.—Moderately free flowering.

*Shape*.—Zygomorphic, single; consisting of three sepals and three petals, one of which is transformed into a labellum; the two lateral petals not overlapping or slightly overlapping the dorsal sepal and moderately overlapping the lateral sepals; lateral sepals touching one another.

*Aspect*.—Flowers are outward-facing to slightly nodding.

*Vertical height*.—Approximately 10.7 cm.

*Diameter*.—Approximately 10.9 cm.

*Depth*.—Approximately 4.8 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 5.2 cm. Width — Approximately 4.6 cm. Shape — Obovate to short spatulate. Apex — Obtuse. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — White, nearest to RHS NN155D, and suffused with violet towards the apex, nearest to RHS N87D but lighter; heavily dotted purple, nearest to RHS N77A; base of the petal is blotched with purple, nearest to RHS N79A. Color when opening, lower surface — White, nearest to RHS NN155D, and suffused with purple-violet towards the apex, nearest to in between RHS N82C and N82D; dots from upper surface can be seen from the lower surface; nearest to RHS N77A. Color when fully opened, upper surface — White, nearest to RHS NN155D, and suffused with violet, nearest to RHS 85D; heavily suffused with a darker violet towards the apex, nearest to a mixture of RHS N87A, N87B and N87C; heavily dotted purple, nearest to N77A but darker; base of the petal is blotched with purple, nearest to RHS N79A. Color when fully opened, lower surface — Violet, nearest to in between RHS 85C and 85D, and fading to violet towards the apex, nearest to a combination of RHS N88C, N88D, and 86C. Fading, upper surface — Not fading. Fading, lower surface — Not fading. Venation — Densely reticulate. Venation color, fully opened, upper surface — White, nearest to RHS NN155D, and suffused with violet, nearest to RHS 85D; heavily suffused with a darker violet towards the apex, nearest to a mixture of RHS N87A, N87B and N87C; heavily dotted purple, nearest to N77A but darker; base of the petal is blotched with purple, nearest to RHS N79A. Venation color, fully opened, lower surface — Violet, nearest to RHS N82C.

*Labellum*.—Shape — Three-lobed; the shape of the lateral lobes is ovate, and the aspect is involute; the shape of the central lobe is oblong, and the aspect is strongly revolute. Length — Central lobe — Approximately 2.1 cm. Lateral lobes — Approximately 0.7 cm. Width — Central lobe — Approximately 1.2 cm. Lateral lobes — Approximately 0.8 cm. Apex — Central lobe — Emarginate. Lateral lobes — Obtuse. Base — Central lobe — Cuneate. Lateral lobes — Cuneate. Margin — Central lobe — Entire; slightly undulated. Lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — Purple-violet, nearest to RHS N81A; apex is purple, nearest to RHS 79A. Lateral lobes — Green-white, nearest the RHS 157B; dotted purple and purple-violet at the base, nearest to RHS 79A and N81A respectively; based suffused with yellow-orange, nearest to RHS 15A. Color when opening, lower surface — Central lobe — Purple, nearest to RHS 79A, and fading lighter towards the base, nearest to RHS 76D. Lateral lobes — Green-white, nearest the RHS 157D, and lightly suffused with purple-violet towards the base, nearest to RHS N81C. Color when fully opened, upper surface — Central lobe — Purple-violet, nearest to RHS N81A; apex is purple, nearest to RHS 79A. Lateral lobes —

Greyed-yellow, nearest the RHS 160D; dotted purple and purple-violet at the base, nearest to RHS 79A and N81A respectively; based suffused with yellow-orange, nearest to RHS 15A. Color when fully opened, lower surface — Central lobe — Purple, nearest to RHS 79A, and fading lighter towards the base, nearest to RHS 76D. Lateral lobes — Green-white, nearest the RHS 157D, and lightly suffused with purple-violet towards the base, nearest to RHS N81C. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities*.—Dimensions — 1.7 cm long and 0.7 cm wide, on average. Color — Purple-violet, nearest to RHS N81A, and fading to white towards the proximal end, nearest to RHS 155A.

*Spurs*.—Quantity — Average of 1. Length — Approximately 0.8 cm. Diameter — Approximately 0.3 cm. Vertical height — Approximately 0.6 cm, at the base. Shape — Short triangular; flattened. Apex — Bluntly acute. Base — Broad cuneate. Pubescence, texture and luster — Glabrous, smooth, and matte. Color — Purple, nearest to RHS 76C; striped a darker shade of purple, nearest to RHS 76A.

*Sepals*.—Quantity — Average of 3 unfused sepals. Arrangement — One dorsal sepal and two lateral sepals. Length — Dorsal sepal — Approximately 5.4 cm. Lateral sepals — Approximately 5.7 cm. Width — Dorsal sepal — Approximately 5.0 cm. Lateral sepals — Approximately 5.4 cm. Shape — Dorsal sepal — Broad ovate. Lateral sepals — Broad ovate. Apex — Dorsal sepal — Obtuse. Lateral sepals — Obtuse. Base — Dorsal sepal — Cuneate. Lateral sepals — Cuneate. Margin — Dorsal sepal — Entire; moderately undulated. Lateral sepals — Entire; moderately undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — White, nearest to RHS NN155D, and suffused with violet towards the apex, nearest to RHS N87D but lighter; heavily dotted purple, nearest to RHS N77A; base of the petal is blotched with purple, nearest to RHS N79A. Lateral sepals — A mixture of yellow-green to white to greyed-yellow, nearest to RHS 150D, 155D and 160D; suffused with a mixture of purple and greyed-purple towards the apex, RHS N77C and N187C; heavily dotted with purple, nearest to RHS N77A. Color when opening, lower surface — Dorsal sepal — White, nearest to RHS NN155D, and suffused with purple-violet towards the apex, nearest to in between RHS N82C and N82D; dots from upper surface can be seen from the lower surface; nearest to RHS N77A. Lateral sepals — Greyed-yellow, nearest to RHS 160D, and suffused with purple towards to apex, nearest to RHS N77D; main vein is purple, nearest to RHS N79D. Color when fully opened, upper surface — Dorsal sepal — White, nearest to RHS NN155D, and suffused with violet, in between RHS 85D; heavily suffused with a darker violet towards the apex, nearest to a mixture of RHS N87A, N87B and N87C; heavily dotted purple, nearest to N77A but darker; base of the petal is blotched with purple, nearest to RHS N79A. Lateral sepals — White, nearest to RHS 155D, and suffused with greyed-yellow, nearest to RHS 159D; suffused with purple towards the margins and apex, nearest to RHS N77C; heavily dotted purple, nearest to in between RHS N77A and 79A. Dots on lateral sepals are larger and more densely distributed on the sepal than those of the dorsal sepal. Color when fully opened, lower surface — Dorsal sepal — Violet, in between RHS 85C and 85D, and suffused with darker violet towards the apex, nearest to a mixture of RHS N88C, N88D, and 86C. Lateral sepals — White, nearest to RHS 155C, and suffused with greyed-yellow, nearest to RHS 160D; suffused with purple towards the margins and apex, nearest to RHS 79D. Fading, upper surface — Not fading. Fading, lower surface — Not fading. Venation — Densely reticulate. Venation color, fully opened, upper surface — Dorsal sepal — No veins visible. Lateral sepals — No veins visible. Venation color, fully opened, lower surface — Dorsal sepal — Violet, nearest to RHS N82C. Lateral sepals — Violet, nearest to RHS N82B.

*Pedicels*.—Length — Approximately 5.9 cm. Diameter — Approximately 0.4 cm. Angle — Approximately 70 degree angle to peduncle axis. Strength — Moderate. Texture — Glabrous, axially angled with 5 "ribs", axially twisted (due to resupination). Luster — Glossy. Color — Purple, nearest to RHS N76A but lighter, and suffused with a slightly darker shade of purple towards the distal end, nearest to RHS 77B.

*Bract*.—Quantity — One bract present at the base of each pedicel. Shape — Reniform; folded around the base of each pedicel. Dimensions — Average of 1.4 cm long and 1.7 cm wide. Apex — Broad acute. Base — Broad cuneate. Margins — Entire. Color, both surfaces — Yellow-green, nearest to RHS 144B.

Reproductive organs:

*Column*.—Length — Approximately 0.7 cm. Diameter — Approximately 0.6 cm. Color — White, nearest to RHS 155A; upper surface suffused with purple, nearest to RHS 76C.

*Ovary*.—Position — Inferior. Diameter — Approximately 1.2 cm. Color — Yellow-green, nearest to RHS 150D.

*Pollinia color*.—Yellow-orange, nearest to RHS 14A.

Seed and fruit: No fruit and seed production has been detected to date.

COMPARISON WITH THE PARENT PLANTS

Plants of the new cultivar 'SPCDW1603' differ from the *Vanda* seed parent, 'M40C2' (not patented), by the characteristics described in Table 1.

TABLE 1

| Characteristic | 'SPCDW1603' | 'M40C2' |
|---|---|---|
| Plant vigor. | More vigorous than 'M40C2'. | Less vigorous than 'SPCDW1603'. |

TABLE 1-continued

| Characteristic | 'SPCDW1603' | 'M40C2' |
|---|---|---|
| Flower size. | Larger than 'M40C2'. | Smaller than 'SPCDW1603'. |
| General coloration of the petals and sepals (excluding the overlaid color pattern) when fully opened. | Darker violet blue. | Lighter violet blue. |
| Color pattern on the petals and sepals. | Heavily dotted with dark purple. | Purple tessellation. |

Plants of the new cultivar 'SPCDW1603' differ from the *Vanda* pollen parent, *Vanda* 'K75' (not patented), by the characteristics described in Table 2.

TABLE 2

| Characteristic | 'SPCDW1603' | 'K75' |
|---|---|---|
| Plant size. | Smaller than 'K75'. | Larger than 'SPCDW1603'. |
| Flower habit. | More floriferous than 'K75'. | Less floriferous than 'SPCDW1603'. |
| Flower size. | Smaller than 'K75'. | Larger than 'SPCDW1603'. |
| General coloration of the petal and sepal color pattern when fully opened. | Lighter violet blue. | Darker violet blue. |
| Luster of the petals and sepals. | Matte, yet slightly shinier than 'K75'. | Matte, duller than 'SPCDW1603'. |

COMPARISON WITH THE MOST SIMILAR *VANDA* CULTIVAR KNOWN TO THE INVENTOR

Plants of the new cultivar 'SPCDW1603' are most similar to the cultivar, *Vanda* 'SPCDW0904' (not protected in the United States; Community Plant Variety Rights grant number 29775). A comparison of 'SPCDW1603' with *Vanda* 'SPCDW0904' is described in Table 3.

TABLE 3

| Characteristic | 'SPCDW1603' | 'SPCDW0904' |
|---|---|---|
| General coloration of the petals and dorsal sepal when fully opened. | Light violet, suffused with a darker violet towards the apex; heavily dotted purple. | Cream with a light purple hue; dotted purple. |
| General coloration of the lateral sepals when fully opened. | Cream and suffused with purple towards the margins and apex; densely dotted purple | Cream with dense dark purple netting. |
| Arrangement of petals. | Free. | Touching. |
| General coloration of the column. | Cream, suffused with purple. | Cream. |

That which is claimed is:

1. A new and distinct variety of *Vanda* plant named 'SPCDW1603', substantially as described and illustrated herein.

* * * * *